(12) United States Patent
Hamlin et al.

(10) Patent No.: US 9,119,799 B2
(45) Date of Patent: Sep. 1, 2015

(54) TRANSDERMAL COMPOSITIONS COMPRISING AN ACTIVE AGENT LAYER AND AN ACTIVE AGENT CONVERSION LAYER

(75) Inventors: Richard Hamlin, Newark, CA (US); Jianye Wen, Palo Alto, CA (US)

(73) Assignee: Teikoku Pharma USA, Inc., San Jose, CA (US)

( * ) Notice: Subject to any disclaimer, the term of this patent is extended or adjusted under 35 U.S.C. 154(b) by 429 days.

(21) Appl. No.: 13/427,602

(22) Filed: Mar. 22, 2012

(65) Prior Publication Data

US 2013/0072884 A1 Mar. 21, 2013

Related U.S. Application Data

(60) Provisional application No. 61/467,337, filed on Mar. 24, 2011.

(51) Int. Cl.
*A61K 9/70* (2006.01)
*A61M 35/00* (2006.01)
*A61K 31/135* (2006.01)

(52) U.S. Cl.
CPC ............... *A61K 9/703* (2013.01); *A61K 9/7061* (2013.01); *A61K 9/7084* (2013.01); *A61K 31/135* (2013.01); *A61M 35/00* (2013.01)

(58) Field of Classification Search
CPC .............................. A61K 9/703; A61K 31/135
USPC ........................................................ 604/304
See application file for complete search history.

(56) References Cited

U.S. PATENT DOCUMENTS

| | | | |
|---|---|---|---|
| 4,452,808 A | 6/1984 | Gallagher | |
| 4,588,740 A | 5/1986 | Gallagher | |
| 4,824,860 A | 4/1989 | Owen | |
| 4,912,126 A | 3/1990 | Owen | |
| 5,176,916 A | 1/1993 | Yamanaka et al. | |
| 5,387,612 A | 2/1995 | Youdim et al. | |
| 5,391,406 A | 2/1995 | Ramharack et al. | |
| 5,422,123 A | 6/1995 | Conte et al. | |
| 5,453,446 A | 9/1995 | Youdim et al. | |
| 5,457,133 A | 10/1995 | Youdim et al. | |
| 5,462,746 A | 10/1995 | Wolter et al. | |
| 5,519,061 A | 5/1996 | Youdim et al. | |
| 5,532,415 A | 7/1996 | Youdim et al. | |
| 5,543,151 A | 8/1996 | Shirai et al. | |
| 5,576,353 A | 11/1996 | Youdim et al. | |
| 5,599,991 A | 2/1997 | Youdim et al. | |
| 5,650,165 A | 7/1997 | Akemi et al. | |
| 5,668,181 A | 9/1997 | Youdim et al. | |
| 5,683,710 A | 11/1997 | Akemi et al. | |
| 5,744,500 A | 4/1998 | Youdim et al. | |
| 5,786,390 A | 7/1998 | Youdim et al. | |
| 5,807,570 A | 9/1998 | Chen et al. | |
| 5,830,497 A | 11/1998 | Yamanaka et al. | |
| 5,891,923 A | 4/1999 | Youdim et al. | |
| 5,972,376 A | 10/1999 | Sendl-Lang et al. | |
| 6,126,968 A | 10/2000 | Peskin et al. | |
| 6,132,761 A | 10/2000 | Muraoka et al. | |
| 6,146,656 A | 11/2000 | Hori et al. | |
| 6,198,017 B1 | 3/2001 | Basedow et al. | |
| 6,218,421 B1 | 4/2001 | King | |
| 6,231,885 B1 | 5/2001 | Carrara | |
| 6,262,330 B1 | 7/2001 | Fujisawa et al. | |
| 6,300,365 B1 | 10/2001 | Holman | |
| 6,316,504 B1 | 11/2001 | Youdim et al. | |
| 6,528,685 B2 | 3/2003 | Cohen et al. | |
| 6,562,363 B1 | 5/2003 | Mantelle et al. | |
| 6,630,514 B2 | 10/2003 | Youdim et al. | |
| 6,638,528 B1 | 10/2003 | Kanios | |
| 6,689,379 B1 | 2/2004 | Bracht | |
| 6,809,120 B1 | 10/2004 | Warrington et al. | |
| 6,929,801 B2 | 8/2005 | Klose et al. | |
| 6,936,661 B2 | 8/2005 | Koch et al. | |
| 6,956,060 B2 | 10/2005 | Youdim et al. | |
| 7,070,808 B2 | 7/2006 | Govil et al. | |
| 7,150,881 B2 | 12/2006 | Govil et al. | |
| 7,175,853 B1 | 2/2007 | Bracht | |
| 7,220,473 B2 | 5/2007 | Beier et al. | |
| 7,335,379 B2 | 2/2008 | Carrara et al. | |
| 7,375,249 B2 | 5/2008 | Boulton et al. | |
| 7,378,439 B2 | 5/2008 | Tarur et al. | |
| 7,396,860 B2 | 7/2008 | Blaugrund et al. | |
| 7,491,847 B2 | 2/2009 | Frenkel et al. | |
| 7,572,834 B1 | 8/2009 | Sterling et al. | |
| 7,598,420 B1 | 10/2009 | Sterling et al. | |
| 7,638,140 B2 | 12/2009 | Govil et al. | |
| 7,989,496 B2 * | 8/2011 | Hartwig et al. | ............... 514/532 |
| 2003/0212085 A1 | 11/2003 | McCall et al. | |

(Continued)

FOREIGN PATENT DOCUMENTS

| | | |
|---|---|---|
| CN | 101032474 B | 2/2011 |
| CN | 102475692 A | 5/2012 |
| EP | 0593807 A1 | 4/1994 |
| EP | 2298277 A1 | 3/2011 |
| WO | 0033812 A2 | 6/2000 |
| WO | 2004012730 A1 | 2/2004 |
| WO | 2009030351 A2 | 3/2009 |
| WO | 2009152777 A1 | 12/2009 |

OTHER PUBLICATIONS

Am et al., "Contrasting neuroprotective and neurotoxic actions of respective metabolites of Anti-Parkinson drugs rasagiline and selegiline." Neuroscience Letters 355 (2004) 169-172.*

*Primary Examiner* — Walter Webb

(74) *Attorney, Agent, or Firm* — Bret E. Field; Khin Chin; Bozicevic, Field & Francis LLP

(57) ABSTRACT

Transdermal compositions are provided. Aspects of the transdermal compositions include: an active agent layer and a conversion layer, where the conversion layer includes a weak base and, optionally, a carboxylated component. Also provided are methods of using the transdermal compositions and kits containing the transdermal compositions.

21 Claims, 6 Drawing Sheets

(56) References Cited

U.S. PATENT DOCUMENTS

| | | |
|---|---|---|
| 2004/0013620 A1 | 1/2004 | Klose et al. |
| 2004/0253299 A1 | 12/2004 | Beier et al. |
| 2005/0175680 A1 | 8/2005 | Morgan et al. |
| 2005/0186141 A1 | 8/2005 | Gonda |
| 2005/0187283 A1 | 8/2005 | Drago |
| 2005/0191348 A1 | 9/2005 | Youdim et al. |
| 2005/0267176 A1 | 12/2005 | Barberich |
| 2006/0078604 A1 | 4/2006 | Kanios et al. |
| 2006/0188581 A1 | 8/2006 | Peskin et al. |
| 2007/0026054 A1 | 2/2007 | Theobald et al. |
| 2007/0078172 A1 | 4/2007 | McElroy et al. |
| 2007/0093495 A1 | 4/2007 | Ruggero et al. |
| 2007/0225379 A1 | 9/2007 | Carrara et al. |
| 2007/0254941 A1 | 11/2007 | Kumar et al. |
| 2008/0004329 A1 | 1/2008 | Jamieson et al. |
| 2008/0089859 A1 | 4/2008 | Homan |
| 2008/0161408 A1 | 7/2008 | Frenkel et al. |
| 2008/0220092 A1 | 9/2008 | Dipierro et al. |
| 2008/0292708 A1 | 11/2008 | Stefanelli et al. |
| 2009/0035377 A1 | 2/2009 | Houze |
| 2009/0043111 A1 | 2/2009 | Liu |
| 2009/0062400 A1 | 3/2009 | Oron et al. |
| 2009/0076160 A1 | 3/2009 | Lendvai et al. |
| 2009/0136549 A1 | 5/2009 | Lin et al. |
| 2009/0136555 A1 | 5/2009 | Crowley et al. |
| 2009/0155343 A1 | 6/2009 | Kawahara et al. |
| 2009/0291127 A1 | 11/2009 | Wen et al. |
| 2010/0010095 A1 | 1/2010 | Frenkel |
| 2010/0016442 A1 | 1/2010 | Cohen et al. |
| 2010/0029987 A1 | 2/2010 | Allegrini et al. |
| 2010/0040690 A1 | 2/2010 | Govil et al. |
| 2010/0087768 A1 | 4/2010 | Forlano et al. |
| 2011/0002976 A1 | 1/2011 | Yamamoto et al. |
| 2012/0265158 A1 * | 10/2012 | Braun et al. .................. 604/307 |
| 2014/0170208 A1 | 6/2014 | Braun et al. |

* cited by examiner

1 Backing
2 Converting layer or drug layer
3 Structural support and/or membrane
4 Drug layer or converting layer
5 Release liner

TRANSDERMAL COMPOSITIONS COMPRISING AN ACTIVE AGENT LAYER AND AN ACTIVE AGENT CONVERSION LAYER

CROSS-REFERENCE TO RELATED APPLICATIONS

Pursuant to 35 U.S.C. §119 (e), this application claims priority to the filing dates of: U.S. Provisional Patent Application Ser. No. 61/467,337 filed on Mar. 24, 2011; the disclosure of which application is herein incorporated by reference.

INTRODUCTION

There is a constant need to administrate physiologically active agents, such as anti-Parkinson agents, into human body. Oral administration is the most commonly used method because it is relatively simple to do. However, the oral administration route is often complicated with gastrointestinal irritation and drug metabolism in the liver.

Administration through human skin (transdermal drug delivery) is an alternative route to oral administration and can provide some advantages such as the avoidance of first pass metabolism, controlled delivery, more simple dosing regime, and better patient compliance. Transdermal active agent compositions, also known as transdermal patches or skin patches, are adhesive patches containing an active agent that are placed on the skin to deliver the active agent through the skin. Transdermal patches deliver the active agent by percutaneous absorption, which is the absorption of substances through unbroken skin. After a transdermal patch is applied to the skin, the active agent contained in the patch passes through, or permeates the skin and can reach its site of action through a systemic blood flow. Alternatively, the transdermal patch may be placed on the desired treatment site such that the medication contained in the patch is delivered topically.

One major drawback of transdermal route is the limitation of the amount of drug that can be transported across the skin. In order to increase the amount of drug going through skin, drug molecules in free base form are typically used in transdermal route. Drug in free base form is usually not as stable as drug in salt form. Therefore, stability of drug in transdermal formulations often causes concern. Another approach to increase skin permeation is to use chemical enhancers in the formulation. While delivery through skin can often be increased with the use of enhancers, they often induce more skin irritation.

SUMMARY OF INVENTION

Figure 1A:
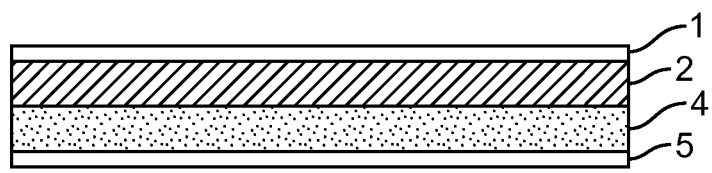
FIGS. 1A and 1B show cross sectional views of two different embodiments of the transdermal active agent formulation in accordance with the invention.

Transdermal compositions are provided. Aspects of the transdermal compositions include: an active agent layer and a conversion layer, where the conversion layer includes a weak base and, optionally, a carboxylated component. Also provided are methods of using the transdermal compositions and kits containing the transdermal compositions.

DETAILED DESCRIPTION

Transdermal compositions are provided. Aspects of the transdermal compositions include: an active agent layer and a conversion layer, where the conversion layer includes a weak base and, optionally, a carboxylated component. Also provided are methods of using the transdermal compositions and kits containing the transdermal compositions.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various embodiments of the invention, aspects of the transdermal compositions are reviewed first in greater detail, followed by a detailed description of embodiments of using the transdermal delivery systems and a review of kits that include the transdermal delivery systems.

Transdermal Compositions

As summarized above, transdermal compositions are provided. Transdermal compositions of the invention are formulations that are configured to transdermally deliver an active agent to a subject when topically applied to a skin surface of a subject. The compositions of the invention include two or more layers, where the two or more layers include at least an active agent layer and a conversion layer, wherein the two or more layers are configured to provide for multi-day delivery of a therapeutically effective amount of an active agent to a subject when the composition is topically applied to said subject.

By multi-day delivery is meant that the layer is formulated to provide a therapeutically effective amount of the active agent to a subject when the composition is applied to a skin site of a subject for a period of time that is 1 day or longer, such as 2 days or longer, e.g., 3 days or longer, such as 5 days or longer, including 7 days or longer, such as 10 days or longer. By therapeutically effective amount is meant that the compositions, when applied to a skin site of a subject during its intended time of application, e.g., within 7 days of application, provides for a systemic amount of active agent that provides a desired therapeutic activity. In some embodiments, the compositions provide delivery of a target dosage of active agent that is 0.5 mg/day or greater over a one week period (i.e., 7 days or 168 hours), including 1.0 mg/day or greater over a one week period, such as 10 mg/day or greater over one week.

Transdermal compositions according to certain embodiments of the invention exhibit a substantially constant flux of the active agent, e.g., propynylaminoindan, over an extended period of time. By substantially constant flux is meant that the magnitude of any variation in flux over the extended period of time is 100% variation in flux or less, such as 80% variation in flux or less and including 50% variation in flux or less, e.g., 40% variation in flux or less, 30% variation in flux or less, such as 25% variation in flux or less, such as 20% variation in flux or less, including 15% variation in flux or less, e.g., 10% variation in flux or less. The extended period of time over which substantially constant flux is observed may vary, and in some instances is 24 hours or longer, such as 48 hours or longer, including 72 hours or longer, e.g., 96 hours or longer. While the actual flux may vary, in some instances (e.g., as determined using the skin permeation assay reported in the Experimental Section, below) skin permeation rates of 0.5 $\mu g/cm^2/hr$ or greater, such as 1 $\mu g/cm^2/hr$ or greater, including 10 $\mu g/cm^2/hr$ or greater are provided by the compositions. In some instances, formulations of the invention exhibit substantially reduced burst delivery of agent immediately following application of the formulation to the skin, e.g., as compared to a control formulation in which the pressure sensitive adhesive does not include carboxylated functionality (such as control pressure sensitive adhesives employed in the Experimental Section, below). By substantially reduced burst deliver is meant a reduction of 10% or more, such as 20% or more, e.g., 25% or more, 33% or more, 40% or more, 50% or more, including 66% or more, 75% or more, including 90% or more. In some instances, the formulations are configured to provide substantially zero-order delivery of the active agent.

The size (i.e., area) of the transdermal compositions may vary. In certain embodiments, the size of the composition is chosen in view of the desired transdermal flux rate of the active agent and the target dosage. For example, if the transdermal flux is 3.4 $\mu g/cm^2/hr$ and the target dosage is 5 mg/day, then the transdermal composition is chosen to have an area of about 43 $cm^2$. Or for example, if the transdermal flux is 3.4 $\mu g/cm^2/hr$ and the target dosage is 10 mg/day, then the transdermal patch is chosen have an area of about 87 $cm^2$. In certain embodiments, the compositions have dimensions chosen to cover an area of skin when applied to a skin site that ranges from 10 to 200, such as 20 to 150, including 40 to 140 $cm^2$.

The active agent and conversion layers of the compositions may vary in thickness. In some instances, the combined thickness of the layers ranges from 25 to 250, such as 50 to 200, including 100 to 150 micrometers. The various layers of the composition may have the same thicknesses or different thicknesses, as desired.

In some embodiments, the active agent and conversion layers are insoluble in water. By insoluble in water is meant that that these layers may be immersed in water for a period of 1 day or longer, such as 1 week or longer, including 1 month or longer, and exhibit little if any dissolution, e.g., no observable dissolution.

An aspect of the transdermal compositions according to embodiments of the invention is that they are storage stable. By storage-stable is meant that the compositions may be stored for extended periods of time without significant degradation and/or significant reduction in activity of the active agent. In certain embodiments, the subject compositions are stable for 6 months or longer, such as 1 year or longer, including 2 years or longer, e.g., 3 years or longer, etc., when maintained at 25° C. under sterile conditions. In some cases, the ratio of the amount of active in the composition to the initial amount of active agent in the composition after storage at about 60° C. for at least one month is 92% or more, 93% or more, such as 94% or more, including 95% or more, or greater.

Figure 1B:
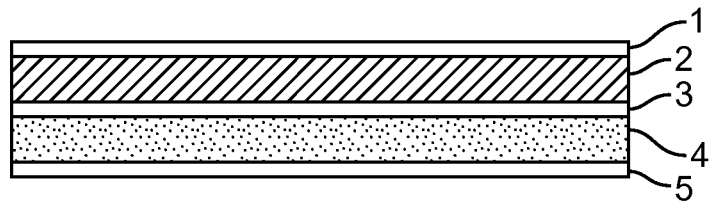

In some embodiments, the compositions of the invention include an active agent layer 4, a converting layer 2, a backing layer 1 and release liner 5, e.g., as shown in FIG. 1A. In some embodiments, the compositions of the invention include an active agent layer 4, a converting layer 2, a support layer/rate controlling membrane 3 separating the active agent and converting layers, a backing layer 1 and release liner 5, e.g., as shown in FIG. 1B. Each of these layers is now described in greater detail.

Active Agent Layer

As reviewed above, transdermal compositions described herein include an active agent layer. Active agent layers of interest include an amount of an active agent present in a matrix. A variety of active agents may be present in the active agent layer. Of interest are active agents that exhibit decreased storage stability in free base form. Such agents may include agents that have a low melting temperature (Tm) in when in base form, e.g., agents having a Tm of 120° C. or lower, such as 90° C. or lower. Agents of interest include agents that have a high vapor pressure when in base form, e.g., agents having a vapor pressure of 0.01 mmHg (25° C.) or higher, such as 0.05 mmHg or higher. A variety of different active agents may be present in the compositions, where such agents include, but are not limited to: propynlaminoindans, e.g., rasagiline; rivastigmine; memantine; aminoesters, e.g., benzocaine, chloroprocaine, cyclomethycain, dimethocaine/larocaine, piperocaine, propoxycaine, procaine/novocaine, proparacaine, tetracaine/amethocaine; aminoamides, such as articaine, bupivacaine, cinchocaine/dibucaine, etidocaine, levobupivacaine, lidocaine/lignocaine, mepivacaine, prilocalne, ropivacaine, trimecaine, etc., and the like In some instances, the active agent present in the active agent layer is a propynylaminoindan. Propynylaminoindans of interest include compounds that are described above the formula:

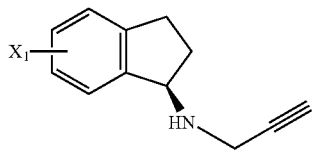

wherein $R_1$ is H, —$OR_2$, or

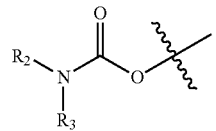

wherein $R_2$ is $C_1$-$C_4$ alkyl, and $R_3$ is H or $C_1$-$C_4$ alkyl. In some instances, the propynylaminoindan is N-propargyl-1-aminoindan (i.e., Rasagiline).

The active agent in the active agent layer, e.g., the propynylaminoindan active agent, may be present in the matrix as a free base or salt, where in certain instances the active agent is present as a salt. Pharmaceutically acceptable salts include, but are not limited to, the mesylate, maleate, fumarate, tartrate, hydrochloride, hydrobromide, esylate, p-toluenesulfonate, benzoate, acetate, phosphate and sulfate salts. In addition, the active agent, e.g., the propynylaminoindan, may be present as a racemic mixture or as a pure enantiomer, such as the R or L enantiomer of the active agent. For example, where the active agent is a propynylaminoindan, the propynylaminoindan in the matrix may solely R(+)—N-propargyl-1-aminoindan free base, while in some instances, the propylnylaminoindan may be solely R(+)—N-propargyl-1-aminoindan mesylate.

The amount of active agent, e.g., propynylaminoindan, present in the active agent layer may vary. In some instances, the amount active agent may range from 5 mg to 50 mg, such as 10 mg to 40 mg and including 15 mg to 30 mg. In some instances, the weight % of the active agent in the active agent layer ranges from 5 to 25%, such as 10 to 20%.

As summarized above, the active agent layer includes an amount of active agent (e.g., as described above) in a matrix. The matrix may vary as desired, where the matrix may be adhesive or non-adhesive. Examples of matrix materials of interest include polymeric materials, where polymeric materials may vary widely and may include, but are not limited to: polyurethanes; ethylene/vinyl acetate copolymers (EVA), polyacrylates, styrenic block copolymers, cellulosic polymers, and the like. Suitable matrix materials may include, but are not limited to, polyacrylates, polysiloxanes, polyisobutylene (FIB), polyisoprene, polybutadiene, styrenic block polymers, blends and combinations of the above, and the like. Suitable styrenic block copolymer-based adhesives include, but are not limited to, styrene-isoprene-styrene block copolymer (SIS), styrene-butadiene-styrene copolymer (SBS), styrene-ethylenebutene-styrene copolymers (SEBS), and di-block analogs thereof. Suitable acrylic polymers are comprised of a copolymer or terpolymer comprising at least two or more exemplary components selected from acrylic acids, alkyl acrylates, methacrylates, copolymerizable secondary monomers or monomers with functional groups. Examples of monomers include, but are not limited to, acrylic acid, methacrylic acid, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, hydroxyethyl acrylate, hydroxypropyl acrylate, acrylamide, dimethylacrylamide, acrylonitrile, dimethylaminoethyl acrylate, dimethylaminoethyl methacrylate, tert-butylaminoethyl acrylate, tert-butylaminoethyl methacrylate, methoxyethyl acrylate, methoxyethyl methacrylate, and the like.

Where desired (e.g., in configurations where the composition is configured such that, during use, the active agent layer contacts the skin), the active agent layer matrix may include a pressure sensitive adhesive. The terms "pressure sensitive adhesive", "self adhesive", and "self stick adhesive" mean an adhesive that forms a bond when pressure is applied to adhere the adhesive with a surface. In some instances, the adhesive is one in which no solvent, water, or heat is needed to activate the adhesive. For pressure sensitive adhesives, the degree of bond strength is proportional to the amount of pressure that is used to apply the adhesive to the surface.

Pressure sensitive adhesives of the active agent layer of interest include, but are not limited to, acrylate copolymers. Acrylate copolymers of interest include copolymers of various monomers which may be "soft" monomers, "hard" monomers, and optionally "functional" monomers. Also of interest are blends including such copolymers. The acrylate copolymers can be composed of a copolymer including bipolymer (i.e., made with two monomers), a terpolymer (i.e., made with three monomers), or a tetrapolymer (i.e., made with four monomers), or copolymers made from even greater numbers of monomers. The acrylate copolymers can include cross-linked and non-cross-linked polymers. The polymers can be cross-linked by known methods to provide the desired polymers.

Monomers from which the acrylate copolymers are produced include at least two or more exemplary components selected from the group including acrylic acids, alkyl acrylates, methacrylates, copolymerizable secondary monomers or monomers with functional groups. Monomers ("soft" and "hard" monomers) of interest include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989). Acrylic adhesives, available from several commercial sources, are sold under the trade names AROSET, DUROTAK, EUDRAGIT, GELVA, and NEOCRYL.

In some instances, the active agent layer may include pressure sensitive adhesive that includes a non-carboxylated polymer, e.g., Gelva 7883, and a carboxylated polymer. For the carboxylated polymer, of specific interest are monomeric residues that provide for —COOH functional groups. Useful carboxylic acid monomers to provide the —COOH functional group may contain from about 3 to about 6 carbon atoms and include, among others, acrylic acid, methacrylic acid, itaconic acid, and the like. Acrylic acid, methacrylic acid and mixtures thereof are employed in certain embodiments. The functional monomer(s) are present in certain embodiments of the copolymers in an amount of 2 wt % or more, such as between 3-10 wt %.

In some embodiments, the active agent adhesive layer may include a pressure sensitive adhesive which is a composition that is, or is substantially the same as, a composition selected from the group consisting of: DuroTak® 87-2100 (Henkel), DuroTak® 87-2852 (Henkel), and the like. The term "substantially the same" as used herein refers to a composition that is an acrylate-vinyl acetate copolymer in an organic solvent solution and provides for the functionality as described herein. In some embodiments, the acrylic pressure-sensitive adhesive is selected from the group consisting of DuroTak® 87-2100, DuroTak® 87-2852, and the like. The active agent layer may include a single pressure sensitive adhesive, or a combination of two or more pressure sensitive adhesives.

In some instances, the pressure sensitive adhesive may make up from 50 to 95, such as 60 to 90 and including 65 to 85% by weight of the matrix.

Conversion Layer

The conversion layer (i.e., converting layer, converting matrix or active agent conversion layer) is a layer that serves to convert the active agent salt in the active agent layer to free base form upon application of the composition to skin. The conversion layer is characterized, at least during storage and prior to skin contact or use, as having substantially less active agent (e.g., 5% by weight or less, such as 2.5% by weight or less, including 1% by weight or less) than the active agent layer, where in some instances the conversion layer includes substantially no active agent (e.g., 0.9% by weight or less, such as 0.5% or less, including no detectable active agent). The conversion layer includes a converting agent, which may be any agent that can mediate the conversion (either alone or in combination with one or more other components) the active agent from salt form to free base form. Converting agents of interest that may be present in the converting layer include weak bases. By weak base is meant a base having a base dissociation constant ($K_b$) of 10 or less, such as 9 or less. Any convenient weak base may be employed, such as polymeric weak bases, e.g., cationic acrylic copolymers, inorganic bases, e.g., calcium hydroxide; etc. Cationic acrylic copolymers of interest are polymers of two or more different monomeric residues, where at least one of the residues is an acrylic residue, e.g., an acrylate or a methacrylate, and at least one of the residues includes a cationic pendant group, e.g., an amino pendant group, where these features may be included in the same or different monomeric residues making up the copolymer. Where desired, the cationic acrylic copolymer may be an aminated methacrylate copolymer. The aminated methacrylate copolymer may be a copolymer of diethylaminoethyl methacrylate, butyl methacrylate and methyl methacrylate. Of interest are aminated methacrylate copolymers that are substantially the same as Eudragit® E100 aminated methacrylate copolymer. As used herein, the term "substantially the same" means that the aminated methacrylate copolymer has the same functional impact on the composition as Eudragit® E100 aminated methacrylate copolymer. In some instances, the aminated methacrylate copolymer is Eudragit® E100 aminated methacrylate copolymer. If present, the amount of cationic acrylic copolymer may be present in an amount ranging from 1 to 15, such as 2 to 10 and including 4 to 8% by weight of the converting layer.

In addition to the converting agent, e.g., weak base, the conversion layer further includes a matrix. In some instances, the matrix is a polymeric matrix, e.g., as described above in connection with the active agent layer.

Where desired (e.g., in configurations where the composition is configured such that, during use, the conversion layer contacts the skin), the conversion layer includes a pressure sensitive adhesive, e.g., as described above. Pressure sensitive adhesives of interest include, but are not limited to carboxylated polymer, such as carboxylated acrylate copolymers. Acrylate copolymers of interest include copolymers of various monomers which may be "soft" monomers, "hard" monomers, and optionally "functional" monomers. Also of interest are blends including such copolymers. The acrylate copolymers can be composed of a copolymer including bipolymer (i.e., made with two monomers), a terpolymer (i.e., made with three monomers), or a tetrapolymer (i.e., made with four monomers), or copolymers made from even greater numbers of monomers. The acrylate copolymers can include cross-linked and non-cross-linked polymers. The polymers can be cross-linked by known methods to provide the desired polymers. Monomers from which the acrylate copolymers are produced include at least two or more exemplary components selected from the group including acrylic acids, alkyl acrylates, methacrylates, copolymerizable secondary monomers or monomers with functional groups. Monomers ("soft" and "hard" monomers) of interest include, but are not limited to, methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989).

Of interest are acrylate copolymers that include polar functional monomeric residues. Of specific interest are monomeric residues that provide for —COOH functional groups. Useful carboxylic acid monomers to provide the —COOH functional group may contain from about 3 to about 6 carbon atoms and include, among others, acrylic acid, methacrylic acid, itaconic acid, and the like. Acrylic acid, methacrylic acid and mixtures thereof are employed in certain embodiments. The functional monomer(s) are present in certain embodiments of the copolymers in an amount of 2 wt % or more, such as between 3-10 wt %.

In some embodiments, the adhesive may have a composition that is, or is substantially the same as, a composition selected from the group consisting of: DuroTak® 87-2100 (Henkel), DuroTak® 87-2852 (Henkel), and the like. The term "substantially the same" as used herein refers to a composition that is an acrylate-vinyl acetate copolymer in an organic solvent solution and provides for the functionality as described herein. In some embodiments, the acrylic pressure-sensitive adhesive is selected from the group consisting of DuroTak® 87-2100, DuroTak® 87-2852, and the like. The converting layer may include a single pressure sensitive adhesive, or a combination of two or more pressure sensitive adhesives. The pressure sensitive adhesive may be the same as or different from that present in the active agent layer.

In some instances, the pressure sensitive adhesive may make up from 50 to 95, such as 60 to 90 and including 65 to 85% by weight of the matrix.

In addition to the weak base, the conversion layer may optionally include a carboxylated component. By carboxylated component is meant a component of the layer, e.g., the matrix or an additional compound in the matrix, that has a carboxyl moiety. As such, in some instances the carboxylated component is a polymeric component, such as a matrix component, e.g., a carboxylated polymer of a pressure sensitive adhesive, such as described above. Additionally or alternatively, the carboxylated component may be some other compound present in the conversion layer, such as small molecule, e.g., an organic acid, e.g., ascrobic acid.

Permeation Enhancer

At least one of the active agent layer and the conversion layer, e.g., as described herein, may contain a percutaneous absorption enhancer. The percutaneous absorption enhancer may facilitate the absorption of the active agent by the skin of the subject. The percutaneous absorption enhancer may also be referred to as a percutaneous permeation enhancer because it may facilitate not only the percutaneous absorption of the active agent, but also the percutaneous permeation of the active agent through the skin of the subject. The percutaneous absorption enhancer may include, but is not limited to the following: aliphatic alcohols, such as but not limited to saturated or unsaturated higher alcohols having 12 to 22 carbon atoms, such as oleyl alcohol and lauryl alcohol; fatty acids, such as but not limited to linolic acid, oleic acid, linolenic acid, stearic acid, isostearic acid and palmitic acid; fatty acid esters, such as but not limited to isopropyl myristate, diisopropyl adipate, and isopropyl palmitate; alcohol amines, such as but not limited to triethanolamine, triethanolamine hydrochloride, and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —O—$CH_2CH_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as but not limited to glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include, but are not limited to octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols; lactic acid alkyl esters; dibasic acid alkyl esters; acylated amino acids; pyrrolidone; pyrrolidone derivatives; and combinations thereof.

Additional types of percutaneous absorption enhancers include, but are not limited to lactic acid, tartaric acid, 1,2,6-hexanetriol, benzyl alcohol, lanoline, potassium hydroxide (KOH), and tris(hydroxymethyl)aminomethane.

Specific examples of percutaneous absorption enhancers include, but are not limited to glycerol monooleate (GMO), sorbitan monolaurate (SML), sorbitan monooleate (SMO), laureth-4 (LTH), and combinations thereof.

In some cases, the matrix of at least one of the active agent layer and the converting layer contains the percutaneous absorption enhancer in an amount ranging from 2% to 25% (w/w), such as from 5% to 20% (w/w), and including from 5% to 15% (w/w). In certain cases, the matrix contains the percutaneous absorption enhancer in an amount of about 5% (w/w), about 10% (w/w), about 15% (w/w), or about 20% (w/w).

Where desired, antioxidants, such as BHA, BHT, propyl gallate, pyrogallol, tocopherol, etc. may also be incorporated into any one or all of the layers.

Structural Support/Rate-Controlling Membrane

In some embodiments, the transdermal formulations include an intermediate layer, e.g., non-woven PET, microporous polypropylene, etc., positioned between the active agent layer and the conversion layer. In some embodiments, the intermediate layer may be a rate-controlling membrane. The rate-controlling membrane meters the quantity of active agent that is administered through the skin for a prolonged period of time, such that the active agent is released from the transdermal formulation at a substantially constant rate until the desired total quantity (i.e., target dosage) of active agent is administered.

In certain embodiments, the rate-controlling membrane may be a microporous membrane having pores that allow permeation of the active agent. In these embodiments, the flux or release rate of the active agent by the membrane is controlled by the rate of which the active agent is able to diffuse through the pores of the membrane. The rate-controlling membrane may be any porous material that permits the permeation of the active agent, such as but not limited to polypropylene, polyethylene, polyacrylonitrile, polytetrafluoroethylene, polydimethylsiloxane, polymethyl methacrylate, and combinations thereof. Additionally, the rate-controlling membrane may be single layer or multi-layer (i.e., having one or more microporous membrane layers composed of the same or different material laminated together). In certain embodiments, the rate-controlling membrane is a monolayer polypropylene membrane.

The porosity, pore size and thickness of the rate-controlling membrane depend on the physicochemical properties, such as the molecular weight of the active agent, the flux required, and the like. For example, the rate-controlling membrane may typically have the following properties: a porosity ranging from about 10% to 85%, including from about 20% to 75%, such as from 30% to 50%; a pore size ranging from 0.03-0.25 μm×μm, including 0.03-0.2 μm×μm, such as 0.04-0.12 μm×μm; and a thickness ranging from 10 μm to 70 μm, including from 15 μm to 60 μm, such as from 20 μm to 50 μm. In certain embodiments, the rate-controlling membrane may have a porosity of 37%, a pore size of 0.04-0.12 μm×μm, and a thickness of 25 μm.

In some embodiments, the rate-controlling membrane may have a composition that is substantially the same as the composition of Celgard® 2400 (Celgard LLC, Charlotte, N.C.). The term "substantially the same" as used herein refers to a composition that is a monolayer polypropylene membrane and provides for the functionality as described herein. In some embodiments, the rate-controlling membrane is Celgard® 2400.

Multi-Layer Structure

As summarized above, the transdermal compositions described herein have a multi-layer structure. By multi-layer structure is meant that the compositions include two or more distinct layers of differing composition, in addition to the backing (e.g., as described below), where the total number of distinct layers in the composition may be two or more, such as 3 or more, including 4 or more, e.g., 5 or more. In some instances, the number of distinct layers may range from 2 to 5, such as 2 to 4, including 2 to 3. For example, one may have a configuration in which a converting layer is present between first and second conversion layers. As mentioned above, the thicknesses of each of the layers in the composition may be the same or different, as desired.

Backing

As summarized above, transdermal compositions of interest may include a backing (i.e., support layer). The backing may be flexible to an extent that it can be brought into close contact with a desired topical location of a subject. The backing may be fabricated from a material that it does not absorb the active agent, and does not allow the active agent to be released from the side of the support. The backing may include, but is not limited to, non-woven fabrics, woven fabrics, films (including sheets), porous bodies, foamed bodies, paper, composite materials obtained by laminating a film on a non-woven fabric or fabric, and combinations thereof.

Non-woven fabric may include, but is not limited to, the following: polyolefin resins such as polyethylene and polypropylene; polyester resins such as polyethylene terephthalate, polybutylene terephthalate and polyethylene naphthalate; rayon, polyamide, poly(ester ether), polyurethane, polyacrylic resins, polyvinyl alcohol, styrene-isoprene-styrene copolymers, and styrene-ethylene-propylene-styrene copolymers; and combinations thereof. Fabrics may include, but are not limited to: cotton, rayon, polyacrylic resins, polyester resins, polyvinyl alcohol, and combinations thereof. Films may include, but are not limited to the following: polyolefin resins such as polyethylene and polypropylene; polyacrylic resins such as polymethyl methacrylate and polyethyl methacrylate; polyester resins such as polyethylene terephthalate, polybutylene terephthalate and polyethylene naphthalate; and besides cellophane, polyvinyl alcohol, ethylene-vinyl alcohol copolymers, polyvinyl chloride, polystyrene, polyurethane, polyacrylonitrile, fluororesins, styrene-isoprene-styrene copolymers, styrene-butadiene rubber, polybutadiene, ethylene-vinyl acetate copolymers, polyamide, and polysulfone; and combinations thereof. Papers may include, but are not limited to, impregnated paper, coated paper, wood free paper, Kraft paper, Japanese paper, glassine paper, synthetic paper, and combinations thereof. Composite materials may include, but are not limited to, composite materials obtained by laminating the above-described film on the above-described non-woven fabric or fabric.

The size of the backing may vary, and in some instances the backing is sized to cover the desired topical target site. In some embodiments, the backing has a length ranging from 2 to 100 cm, such as 4 to 60 cm and a width ranging from 2 to 100 cm, such as 4 to 60 cm.

In some embodiments, the backing layer is insoluble in water. By insoluble in water is meant that that the backing layer may be immersed in water for a period of 1 day or longer, such as 1 week or longer, including 1 month or longer, and exhibit little if any dissolution, e.g., no observable dissolution.

The backing layer may be in contact with a surface of the converting layer or the active agent layer, as desired, e.g., depending on whether the composition is configured so that the converting layer or the active agent layer contacts the skin upon application to a subject. For example, where the composition is configured so that the active agent layer contacts the skin upon application, the backing will be in contact with a surface of the active agent layer. Alternatively, where the composition is configured so that the converting layer contacts the skin upon application, the backing will be in contact with a surface of the converting layer.

Release Liner

In some embodiments, a release liner is provided on the active agent layer (i.e., matrix), and specifically on a surface of the active agent layer that is distal (i.e. opposite) from the backing layer, if present. The release liner facilitates the protection of the active agent layer. The release liner may be prepared by treating one side of polyethylene-coated wood free paper, polyolefin-coated glassine paper, a polyethylene terephthalate (polyester) film, a polypropylene film, or the like with a silicone treatment. The release liner may be in contact with a surface of the converting layer or the active agent layer, as desired, e.g., depending on whether the composition is configured so that the converting layer or the active agent layer contacts the skin upon application to a subject. For example, where the composition is configured so that the active agent layer contacts the skin upon application, the release liner will be in contact with a surface of the active agent layer. Alternatively, where the composition is configured so that the converting layer contacts the skin upon application, the release liner will be in contact with a surface of the converting layer.

Methods of Use

Methods of using the product transdermal compositions include administering an effective amount of the active agent to a subject in order to treat the subject for a target condition of interest, e.g., as described in the Utility section below. By "treating" or "treatment" is meant at least a suppression or an amelioration of the symptoms associated with the condition afflicting the subject, where suppression and amelioration are used in a broad sense to refer to at least a reduction in the magnitude of a parameter, e.g., symptom, associated with the condition being treated. As such, treatment also includes situations where the condition is completely inhibited, e.g., prevented from happening, or stopped, e.g., terminated, such that the subject no longer experiences the condition. As such, treatment includes both preventing and managing a condition.

In practicing the methods, the transdermal compositions disclosed herein can be topically administered to a subject, i.e., the transdermal compositions may be administered to any convenient topical site (e.g., skin site). Application may include contacting an active agent layer or a converting layer to a skin site of the subject, depending on the configuration of the transdermal composition. Topical sites of interest include both mucosal sites and keratinized skin sites, and therefore include, but are not limited to: mouth, nose, eyes, rectum, vagina, arms, leg, torso, head, etc. The surface area that is covered by the topical composition following application is sufficient to provide for the desired amount of agent administration, and in some embodiments ranges from 1 to 200 cm$^2$, such as from 10 to 180 cm$^2$, and including from 100 to 150 cm$^2$, e.g., 140 cm$^2$.

The transdermal composition may be maintained at the topical site to which it has been applied for a desired amount of time, e.g., to deliver a desired amount of active agent delivery. In some instances, the period of time that the composition is maintained at the site of application is 24 hours or longer, such as 48 hours or longer, e.g., 72 hours or longer, such as 96 hours or longer.

In practicing the subject methods, a given dosage of the transdermal composition may be applied a single time or a plurality of times over a given time period, e.g., the course of the disease condition being treated, where the dosing schedule when a plurality of compositions are administered over a given time period may be daily, weekly, biweekly, monthly, etc.

The area of skin covered by the topical composition when applied may vary. In some instances, the area of skin covered by the topical composition upon application ranges from 1 to 200 cm$^2$, such as 10 to 180 cm$^2$ and including 100 to 150 cm$^2$.

After the transdermal active agent composition has been applied to the skin site for the desired amount of time (i.e., an amount of time sufficient to deliver a target dose of the active agent to the subject over a period of time), the composition may be removed from the skin site. A new transdermal composition may be applied at the same or at a different skin site. The new transdermal composition may be applied to a different skin site to reduce the possible occurrence of skin irritation and/or skin sensitization at the prior site of application.

In certain embodiments, the subject methods include a diagnostic step. Individuals may be diagnosed as being in need of the subject methods using any convenient protocol. In addition, individuals may be known to be in need of the subject methods, e.g., they are suffering from Parkinson's disease. Diagnosis or assessment of target condition can be performed using any convenient diagnostic protocol.

Methods of the invention may further include assessing the efficacy of the treatment protocol that includes administration of the local anesthetic emulsion composition. Assessing the efficacy of treatment may be performed using any convenient protocol.

In some instances, transdermal compositions may be administering in conjunction with one or more additional therapies specific for the target condition of interest. As such, the transdermal compositions may be used alone to treat the target disorder, or alternatively, as in the case of Parkinson's disease, for example, they may be used as an adjunct to the conventional L-DOPA treatments.

Transdermal compositions of the invention may be administered to a variety of different types of subjects. Subjects of interest include, but are not limited to: mammals, both human and non-human, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects, e.g., patients, are humans.

Utility

The transdermal compositions of the invention find use in any application where a subject would benefit from being transdermally administered an active agent, such as a propynylaminoindan, e.g., rasagiline. Rasagiline and/or its salts find use in the treatment of a variety of different disease conditions, such as but not limited to: Parkinson's disease, Alzheimer's Disease, memory disorders, stroke and other disorders, e.g., as described in U.S. Pat. Nos. 5,387,612; 5,453,446; 5,457,133; 5,668,181; 5,576,353; 5,532,415; 5,599,991; 5,786,390; 5,519,061; 5,891,923; 5,744,500 and 6,316,504, the contents of which are hereby incorporated by reference. By treatment is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition.

Kits

Kits for use in practicing certain methods described herein are also provided. In certain embodiments, the kits include one or more transdermal compositions as described above. In certain embodiments, the kits include an adhesive overlay as described above. In some embodiments, the kits include multilayers such as a layer containing drug and a layer that may or may not contain any drug and other excipients. In a given kit that includes two or more compositions, the compositions may be individually packaged or present within a common container.

In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

The following examples are offered by way of illustration and not by way of limitation. Specifically, the following examples are of specific embodiments for carrying out the present invention. The examples are for illustrative purposes only, and are not intended to limit the scope of the present invention in any way.

EXAMPLES

I. Introduction

In certain embodiments, the active agent is a propynylaminoindan, such as rasagiline. Embodiments of the present invention overcome disadvantages of other transdermal rasagiline formulations. Rasagiline has to penetrate across skin in free base form in order to deliver therapeutic effective dose for a sustained period of time, such as up to 7 days. Rasagiline free base is not stable at room temperature and can degrade quickly during room temperature storage. Therefore, the use of rasagiline free base in a formulation is not a feasible option. To address degradation issue, rasagiline in salt form, such as rasagiline mesylate, is employed in formulations of the invention since rasagiline salt typically has higher melting point and is more stable. Since drug in a salt form has very low penetration rate across skin, patches of the invention include a weak base, such as Eudragit or dimethyl triamine, in the formulation to facilitate the conversion of rasagiline salt to base. To further balance the conversion from salt to base to avoid burst delivery, embodiments of the invention may additionally utilize a carboxylated component, such as a pressure sensitive adhesive that contains a carboxylated functionality or a low molecular weight component that includes a carboxylated functionality, e.g., an organic acid. In these embodiments, the interaction between the weak base, active carboxylated component provides for an optimized delivery of the drug, such as rasagiline, across skin.

In formulations according to aspects of the invention, stability of the formulation during storage is improved by configuring the formulation so that conversion of drug to free base upon combination with the weak base is minimized, if not substantially eliminated during storage period. To provide this storage stability, embodiments of the invention employ may employ a multi-layer, e.g., a two-layer, system design. In this configuration, drug is present in one layer (i.e., the active agent layer) and the material that can be used to convert drug from salt form to free base form is provided in a second layer (i.e., the active agent conversion layer). The selection of matrix material and weak base is such that there will be no migration happening during storage period. As soon as the patch is placed on skin, the resultant normal transpiration stream of moisture activates conversion of the salt form of the active agent to free base. To ensure this in certain embodiments of the invention, drug in salt form is used to disperse in a matrix that has low solubility for the drug. Weak base also having low mobility is employed. The novel multilayer, e.g., two-layer, configuration of the transdermal composition can be used not only for rasagiline, but also any drugs that might have the similar stability problems in their free base form.

II. Preparation of Drug Layer and Converting Layer

Formulations were prepared by mixing drug, excipients, and stock solutions adhesives in organic solvents (typically 30-60 wt % solid content in ethyl acetate, and/or methanol, ethanol, toluene), followed by a mixing process. Once a homogeneous mixture was formed, the solution was cast on a release liner (siliconized polyester sheet of 2-3 mils) and dried at 65°-80° C. for 10-90 minutes. The adhesive films were laminated to a PET backing. The final formulations were prepared by laminating drug layer and converting layer together before the flux experiment.

III. Transdermal Flux Tests

Human cadaver skin was used and epidermal layers (stratum corneum and epidermis) were separated from the full-thickness skin as skin membrane. Samples were die-cut with an arch punch to a final diameter of about 2.0 cm². The release liner was removed and the system was placed on top of the epidermis/stratum corneum with the drug adhesive layer facing the stratum corneum. Gentle pressure was applied to effect good contact between the adhesive layer and stratum corneum. The donor and receptor sides of the Franz cell were clamped together and the receptor solution containing a phosphate buffer at pH 6.5 was added to the Franz cell. The cells were kept at 33° C. for the duration of the experiment. Samples of the receptor solution were taken at regular intervals and the active agent concentration was measured by HPLC. The removed receptor solution was replaced with fresh solution to maintain the sink conditions. The flux was calculated from the slope of cumulative amounts of the drug in the receiver compartment versus time plot.

IV. Specific Examples

A. Flux of Rasagiline Mesylate in Acrylate Adhesive: Two Layer Design

Figure 2:
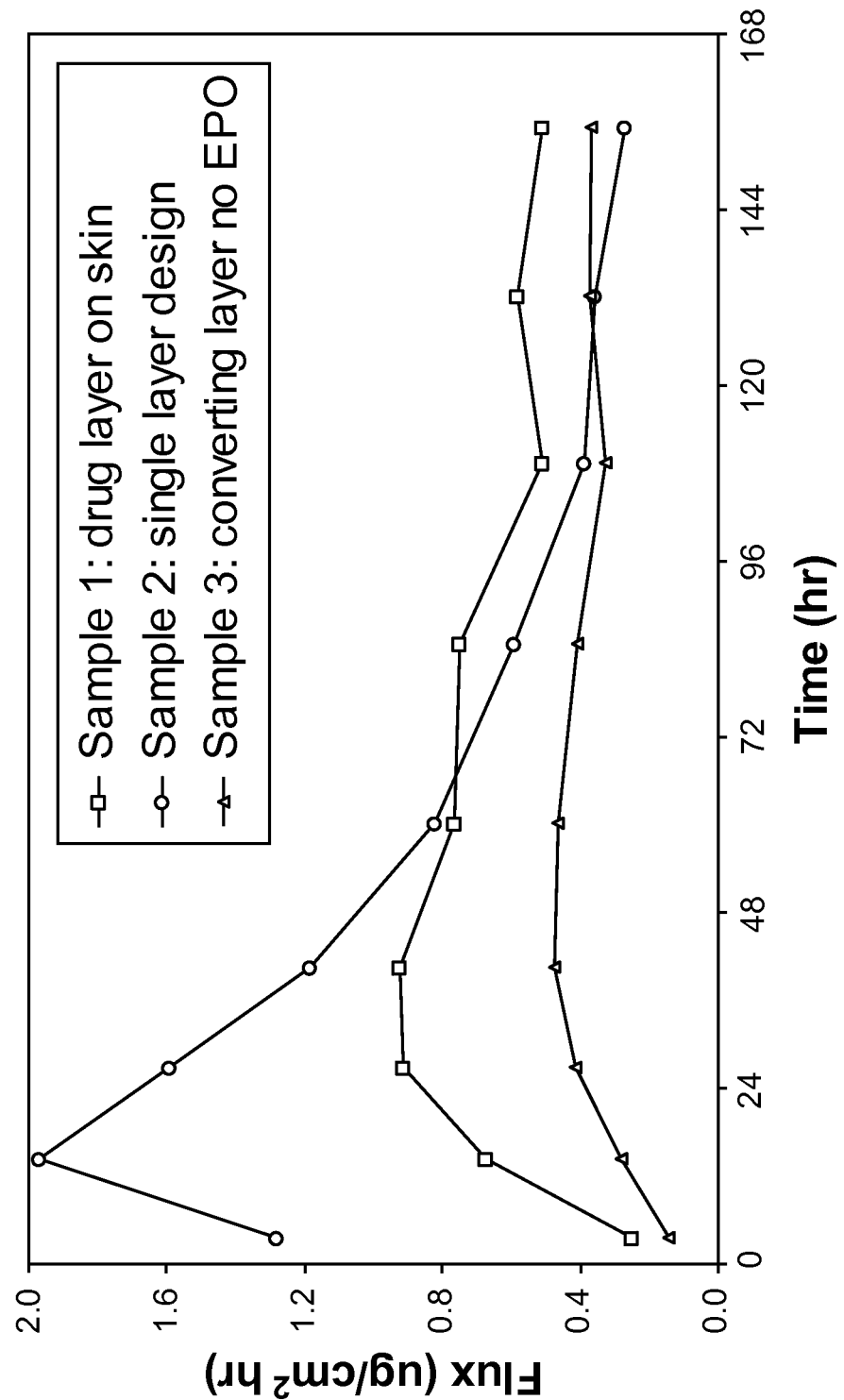
FIGS. 2 to 6 show graphs of flux as a function of time (middle point between the two sampling time points) for various formulations.

Using the general method described previously, a series of transdermal systems were prepared with details shown in following table. The flux through human cadaver skin was measured and the results are graphically presented in FIG. 2. Compared to one layer design, two layer design has lower flux at the beginning and shows a more flat delivery profile. The data also shows that without using converting agent E100, the flux is much lower.

TABLE 1

| Sample | Drug layer | Converting layer | Application/design |
|---|---|---|---|
| 1 | 10% rasagiline mesylate, 3% E100[1] in in Duro-Tak 2100 and Gelva 7883[2] (adhesive ratio 1:3) | None | One layer design with Scotchpak 9723 as backing |
| 2 | 20% rasagiline mesylate in Gelva 7883 | 6% E100 in Duro-Tak 2100 and Gelva 7883 (adhesive ratio 1:3) | Two layer design with Scotchpak 9723 as backing, drug layer in contact with skin |
| 3 | 20% rasagiline mesylate in Gelva 7883 | 0% E100 in Duro-Tak 2100 and Gelva 7883 (adhesive ratio 1:3) | Same as #2 except no E100 in converting layer |

Notes.
1. Both Duro-Tak 2100 (Henkel) and Gelva 7883 (Cytec) are acrylate based pressure sensitive adhesives.
2. E100 is Eudragit E100 (Evonik)

B. Flux of Rasagiline Mesylate in Acrylate Adhesive: Effect of System Design

Figure 3:
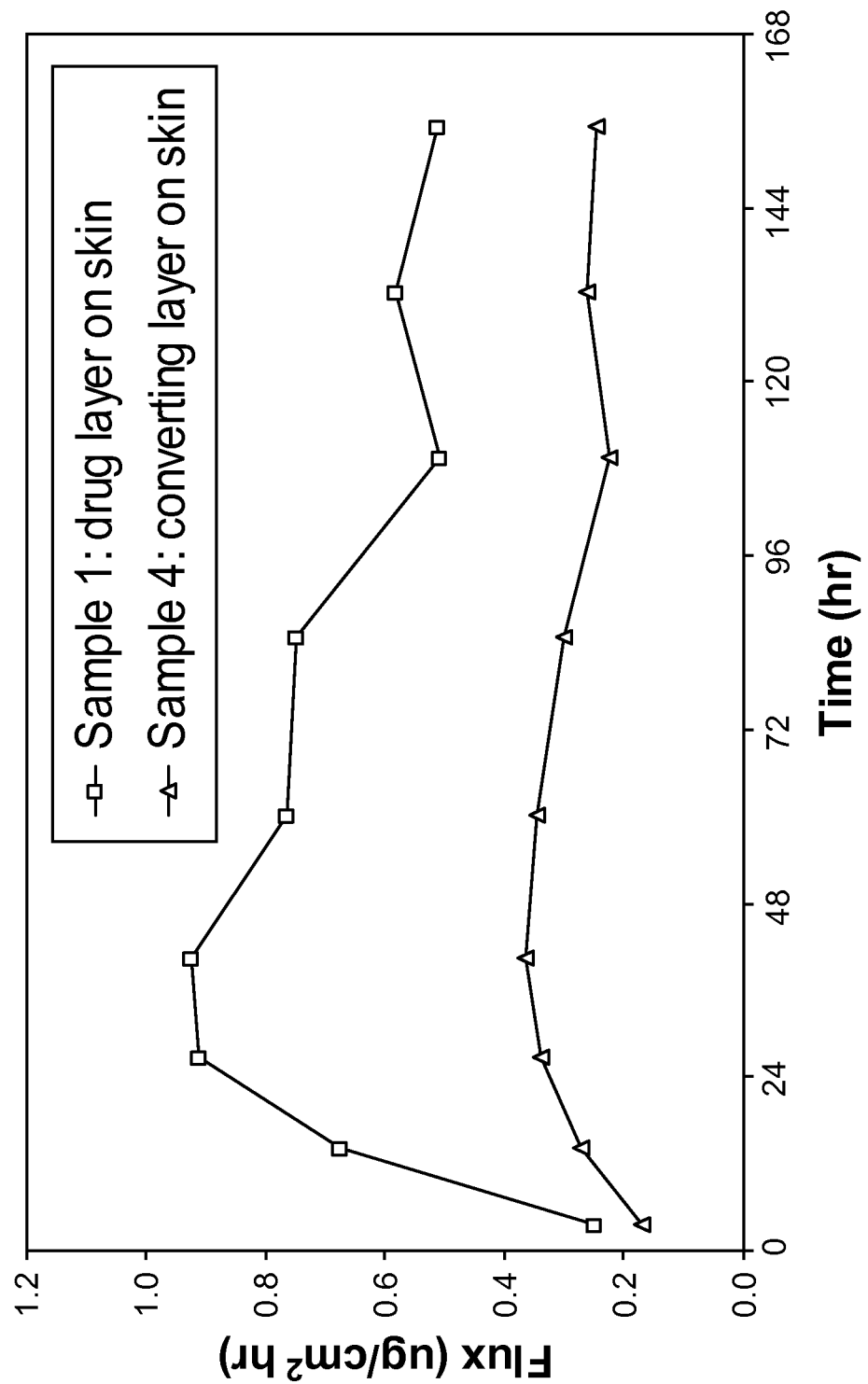

Using the general method described previously, a series of transdermal systems were prepared with details shown in following table. The flux through human cadaver skin was measured and the results are graphically presented in FIG. 3. In this particular experiment, comparison was made between sample with drug layer in contact with skin and converting layer in contact with skin. Higher flux was seen when drug layer is the skin contacting layer.

TABLE 2

| Sample | Drug layer | Converting layer | Application/design |
|---|---|---|---|
| 1 | 20% rasagiline mesylate in Gelva 7883 | 6% E100 in Duro-Tak 2100 and Gelva 7883[1] (adhesive ratio 1:3) | Two layer design with Scotchpak 9723 as backing, drug layer in contact with skin |
| 4 | 20% rasagiline mesylate in Gelva 7883 | 6% E100[2] in Duro-Tak 2100 and Gelva 7883 (adhesive ratio 1:3) | Two layer design with Scotchpak 9723 as backing, converting layer in contact with skin |

Notes.
1. Both Duro-Tak 2100 (Henkel) and Gelva 7883 (Cytec) are acrylate based pressure sensitive adhesives.
2. E100 is Eudragit E100 (Evonik)

C. Flux of Rasagiline Mesylate in Acrylate Adhesive: Effect of Adhesive

Figure 4:
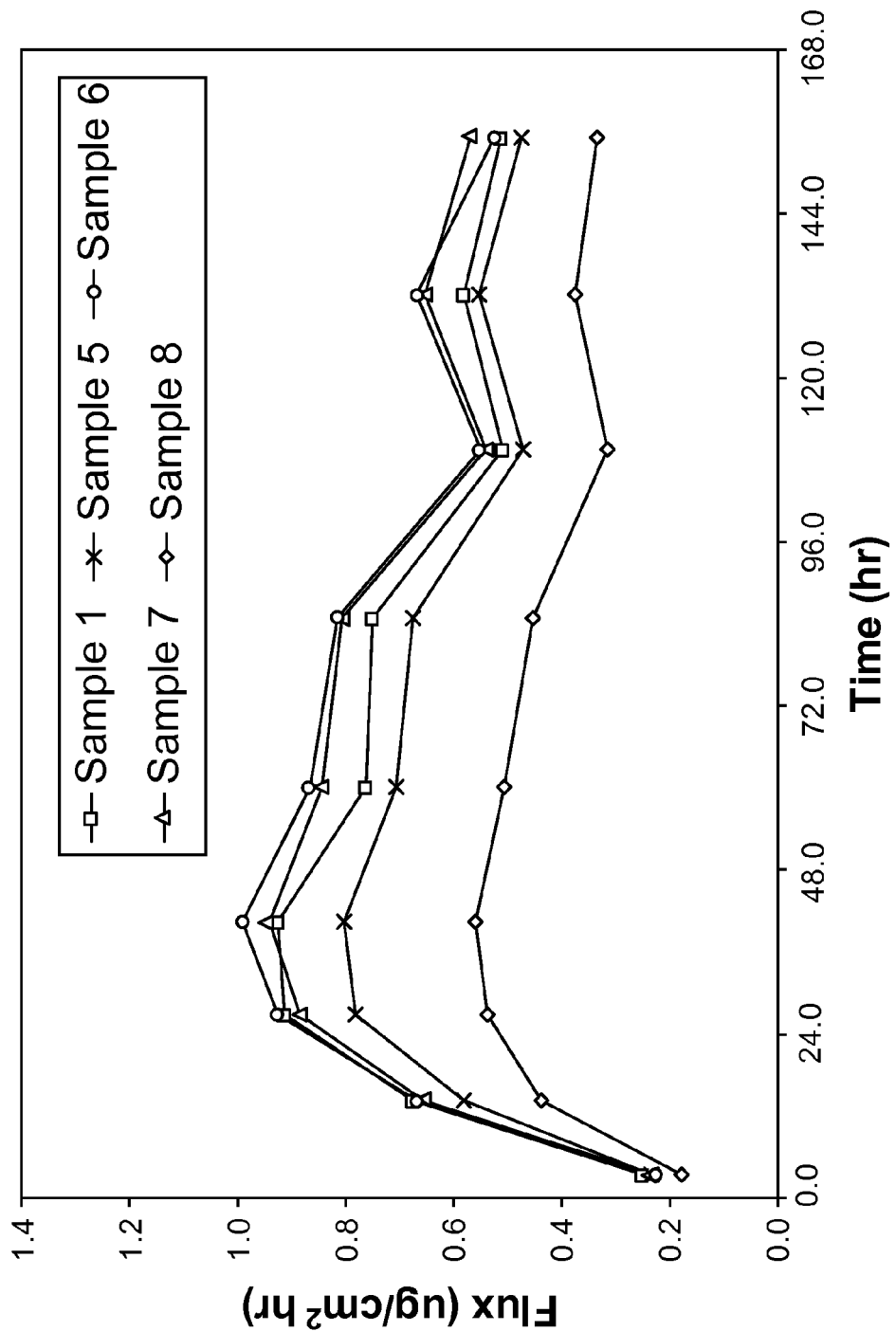

Using the general method described previously, a series of transdermal systems were prepared with details shown in following table. The flux through human cadaver skin was measured and the results are graphically presented in FIG. 4. In this particular experiment, comparison was made between samples with different drug loadings and different adhesive ratios.

TABLE 3

| Sample | Drug layer | Converting layer | Application/design |
|---|---|---|---|
| 1 | 20% rasagiline mesylate in Gelva 7883 | 6% E100 in Duro-Tak 2100 and Gelva 7883 (adhesive ratio 1:3) | Two layer design with Scotchpak 9723 as backing, drug layer in contact with skin |

TABLE 3-continued

| Sample | Drug layer | Converting layer | Application/design |
|---|---|---|---|
| 5 | 20% rasagiline mesylate in Gelva 7883 | 3% E100 in Duro-Tak 2100 and Gelva 7883 (adhesive ratio 1:3) | Two layer design with Scotchpak 9723 as backing, drug layer in contact with skin |
| 6 | 20% rasagiline mesylate in Duro-Tak 2100 and Gelva 7883 (adhesive ratio 1:3) | 6% E100 in Duro-Tak 2100 and Gelva 7883 (adhesive ratio 5:17) | Two layer design with Scotchpak 9723 as backing, drug layer in contact with skin |
| 7 | 20% rasagiline mesylate in Duro-Tak 2100 and Gelva 7883[1] (adhesive ratio 1:3) | 6% E100[2] in Duro-Tak 2100 and Gelva 7883 (adhesive ratio 1:3) | Two layer design with Scotchpak 9723 as backing, drug layer in contact with skin |
| 8 | 10% rasagiline mesylate in Duro-Tak 2100 and Gelva 7883 (adhesive ratio 1:3) | 3% E100 in Duro-Tak 2100 and Gelva 7883 (adhesive ratio 1:3) | Two layer design with Scotchpak 9723 as backing, drug layer in contact with skin |

Notes.
1. Both Duro-Tak 2100 (Henkel) and Gelva 7883 (Cytec) are acrylate based pressure sensitive adhesives.
2. E100 is Eudragit E100 (Evonik)

D. Flux of Rasagiline Mesylate in Acrylate Adhesive: Effect of Loading

Figure 5:
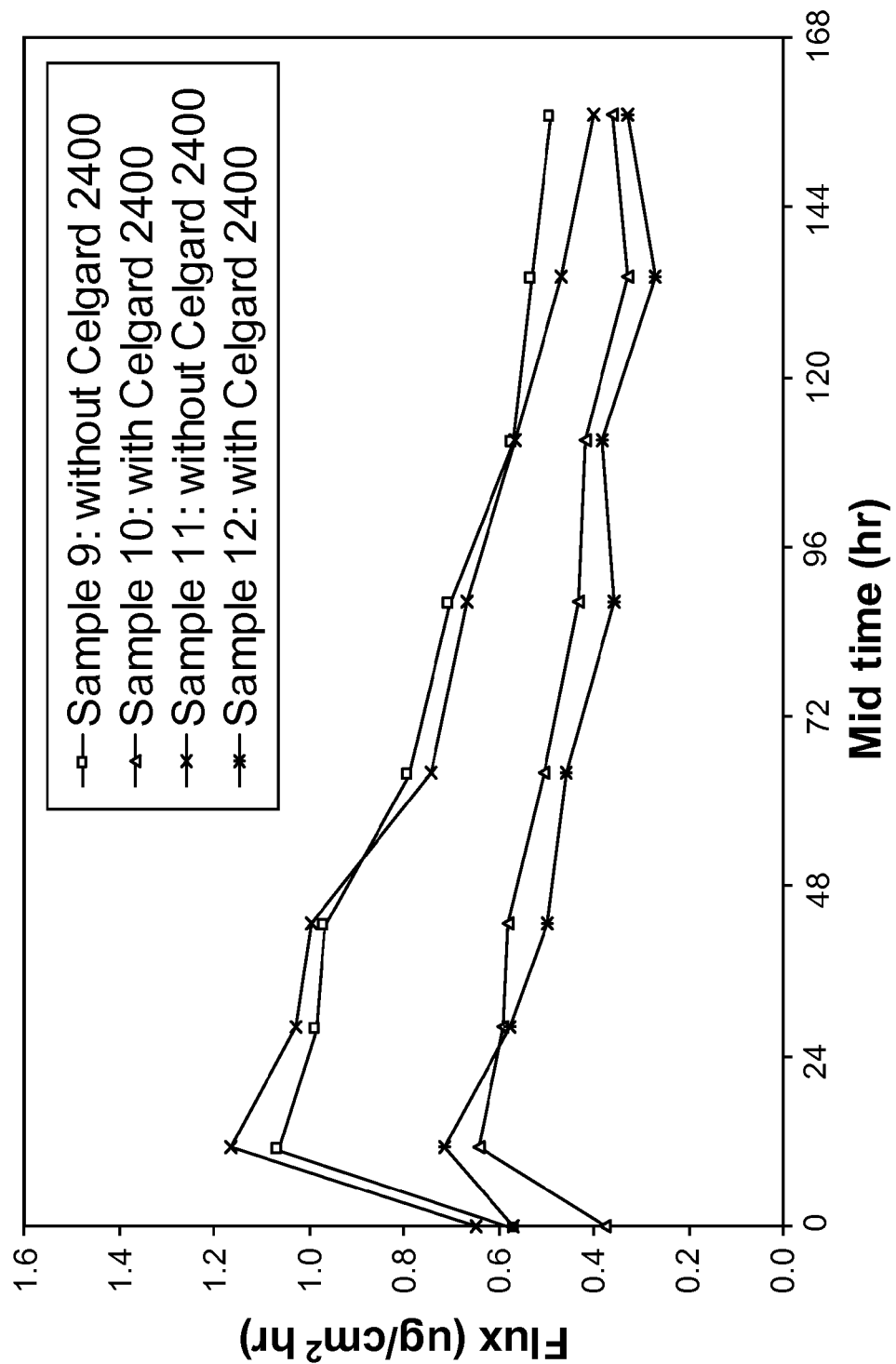

Using the general method described previously, a series of transdermal systems were prepared with details shown in following table. The flux through human cadaver skin was measured and the results are graphically presented in FIG. 5. In this particular experiment, comparison was made between samples with and without a membrane that can serve as both structural support and/or rate control.

TABLE 4

| Sample | Drug layer | Converting layer | Application/design |
|---|---|---|---|
| 9 | 10% rasagiline mesylate in Duro-Tak 2100 and Gelva 7883[1] (adhesive ratio 1:3) | 6% E100[2] in Duro-Tak 2100 and Gelva 7883 (adhesive ratio 1:3) | Two layer design with Scotchpak 9723 as backing, drug layer in contact with skin |
| 10 | 10% rasagiline mesylate in Duro-Tak 2100 and Gelva 7883 (adhesive ratio 1:3) | 6% E100 in Duro-Tak 2100 and Gelva 7883 (adhesive ratio 1:3) | Same as #9 except that there is a Celgard 2400 membrane between two layer |
| 11 | 10% rasagiline mesylate in Gelva 7883 | 6% E100 in Duro-Tak 2100 and Gelva 7883 (adhesive ratio 1:3) | Two layer design with Scotchpak 9723 as backing, drug layer in contact with skin |
| 12 | 10% rasagiline mesylate in Gelva 7883 | 6% E100 in Duro-Tak 2100 and Gelva 7883 (adhesive ratio 1:3) | Same as #9 except that there is a Celgard 2400[3] membrane between two layer |

Notes.
1. Both Duro-Tak 2100 (Henkel) and Gelva 7883 (Cytec) are acrylate based pressure sensitive adhesives.
2. E100 is Eudragit E100 (Evonik)
3. Celgard 2400 is from Celgard and serves as structural support and rate control.

E. Flux of Rasagiline Mesylate in Acrylate Adhesive: Effect of Loading

Figure 6:
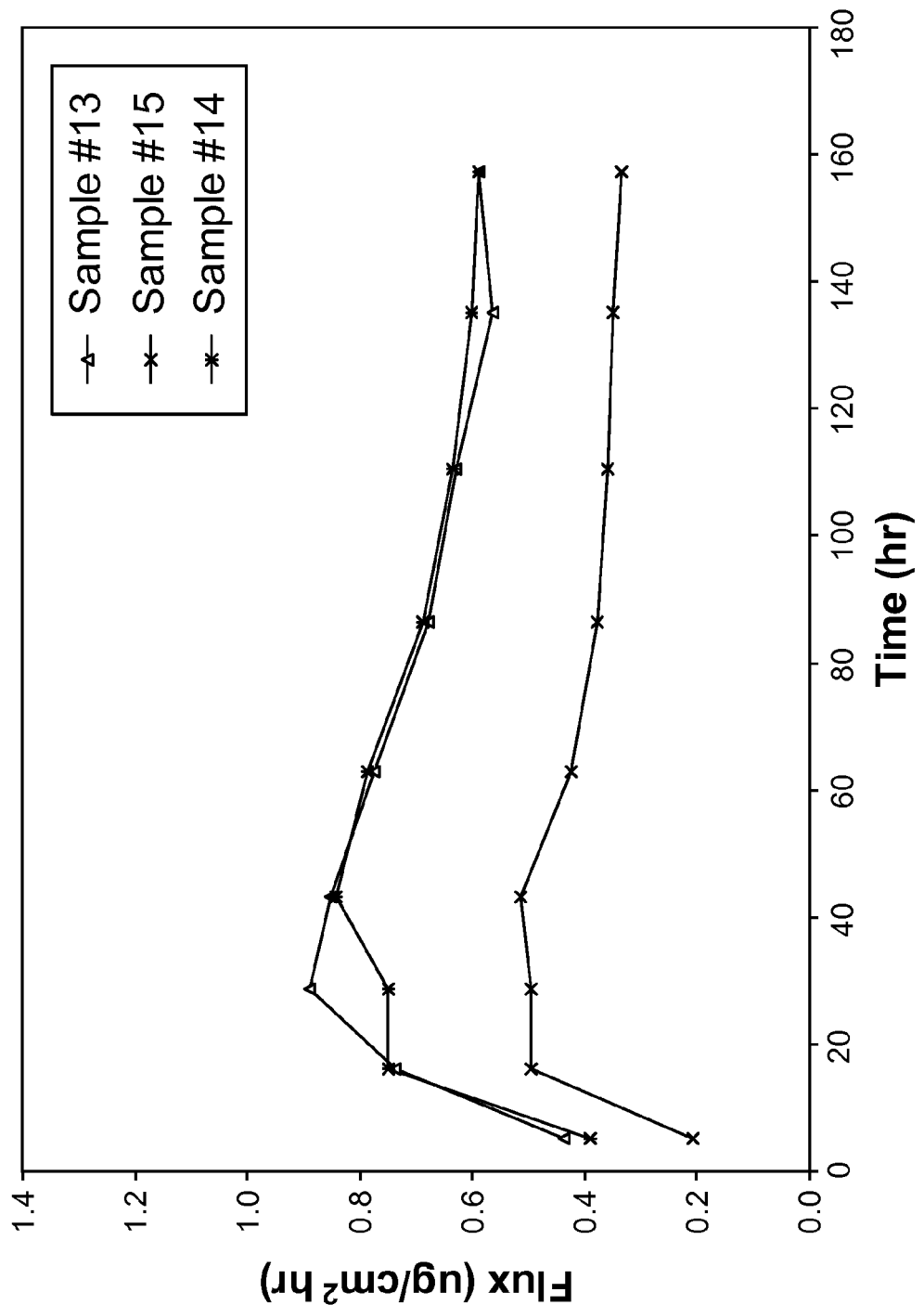

Using the general method described previously, a series of transdermal systems were prepared with details shown in following table. The flux through human cadaver skin was measured and the results are graphically presented in FIG. 6. In this particular experiment, comparison was made between samples with and without the use of converting agent E100.

TABLE 5

| Sample | Drug layer | Converting layer | Application/design |
|---|---|---|---|
| 13 | 10% rasagiline mesylate in Duro-Tak 2100 and Gelva 7883[1] (adhesive ratio 1:3) | 10% E100[2] in Duro-Tak 2100 and Gelva 7883 (adhesive ratio 1:3) | Two layer design with Scotchpak 9723 as backing, drug layer in contact with skin |
| 14 | 10% rasagiline mesylate in Gelva 7883 | 6% E100 in Duro-Tak 2100 and Gelva 7883 (adhesive ratio 1:3) | Two layer design with Scotchpak 9723 as backing, drug layer in contact with skin |
| 15 | 10% rasagiline mesylate in Gelva 7883 | None | One layer design with Scotchpak 9723 as backing and no E100 |

Notes.
1. Both Duro-Tak 2100 (Henkel) and Gelva 7883 (Cytec) are acrylate based pressure sensitive adhesives.
2. E100 is Eudragit E100 (Evonik)

IV. Stability Testing

A two layer patch summarized below was prepared using the protocol described above.

TABLE 6

| Sample | Drug layer | Converting layer | Application/design |
|---|---|---|---|
| 16 | 10% rasagiline mesylate in Gelva 7883[2], 0.5% BHT[3] | 10% E100[2] in Duro-Tak 2052 and Gelva 7883 (adhesive ratio 3:97) | Two layer design with Scotchpak 9723 as backing, drug layer in contact with skin |

Notes.
1. E100 is Eudragit E100 (Evonik)
2. Duro-Tak 2100, Duro-Tak 2052, Duro-Tak 900a, Duro-Tak 9301 (Henkel), Gelva 7883, and Gelva 2999 (Cytec) are acrylate based pressure sensitive adhesives.
3. BHT is anti-oxidant Butylated hydroxytoluene The test patches were prepared at 4 $cm^2$ size, pouched and sealed using Polyacrylonitrile (PAN) material. The patches were stored at in room temperature, 30° C. and 40° C. chambers. At selected time points, the patches were extracted to determine Rasagiline Mesylate and 1-Aminoindan (main degradent) concentration. The stability of the patches was determined by high performance liquid chromatography (HPLC). The results are provided in Table 7, below:

| Con- | T = 0 | | 1 month | | 2 months | | 3 months | |
|---|---|---|---|---|---|---|---|---|
| dition | API | 1-AI | API | 1-AI | API | 1-AI | API | 1-AI |
| RT | 100 (±0.4) | 0.01 | 98.4 (±1.6) | 0.00 | 99.7 (±2.4) | 0.13 | 102.0 (±2.5) | 0.02 |
| 30° C. | — | — | 96.0 (±6.1) | 0.00 | 98.0 (±5.8) | 0.13 | 98.2 (±5.8) | 0.12 |
| 40° C. | — | — | 96.3 (±7.1) | 0.05 | 95.1 (±6.7) | 0.47 | 99.2 (±3.9) | 0.37 |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A transdermal composition comprising:
    an active agent layer comprising a propynylaminoindan in a matrix comprising a non-carboxylated polymer; and
    a conversion layer comprising a weak base in a matrix comprising a carboxylated component.

2. The transdermal composition according to claim 1, wherein the propynylaminoindan is present as a salt.

3. The transdermal composition according to claim 1, wherein the propynylaminoindan is N-propargyl-1-aminoindan.

4. The transdermal composition according to claim 1, wherein the carboxylated component of the conversion layer is an acrylic carboxylated polymer.

5. The transdermal composition according to claim 4, wherein the acrylic carboxylate polymer is an acrylate-vinyl acetate copolymer pressure-sensitive adhesive.

6. The transdermal composition according to claim 1, wherein the carboxylated component of the conversion layer is a low molecular weight organic acid.

7. The transdermal composition according to claim 6, wherein the low molecular weight organic acid is acetic acid.

8. The transdermal composition according to claim 1, wherein the weak base of the conversion layer is a cationic acrylic copolymer.

9. The transdermal composition according to claim 8, wherein the cationic acrylic copolymer is an aminated methacrylate copolymer.

10. The transdermal composition according to claim 9, wherein the aminated methacrylate copolymer is a copolymer of diethylaminoethyl methacrylate, butyl methacrylate and methyl methacrylate.

11. The transdermal composition according to claim 10, wherein the aminated methacrylate copolymer is poly(butyl methacrylate-co-(2-demethylaminoethyl) methacrylate-co-methyl methacrylate).

12. The transdermal composition according to claim 1, wherein the transdermal composition comprises a pressure sensitive adhesive.

13. The transdermal composition according to claim 1, wherein the transdermal composition comprises a permeation enhancer.

14. The transdermal composition according to claim 1, wherein the transdermal composition comprises a rate-controlling layer between the active agent layer and the active agent conversion layer.

15. The transdermal composition according to claim 1, wherein the composition comprises at least one additional layer.

16. The transdermal composition according to claim 1, wherein the transdermal composition exhibits a constant flux of the active agent over an extended period of time.

17. A method comprising:
    applying to a skin surface of a subject a transdermal composition of claim 1
    in a manner sufficient to achieve a constant flux of the active agent over an extended period of time.

18. The method according to claim 17, wherein the extended period of time is 72 hours or longer.

19. The method according to claim 17, wherein the propynylaminoindan is N-propargyl-1-aminoindan.

20. A kit comprising:
    two or more transdermal compositions of claim 1.

21. The transdermal composition according to claim 1, wherein the non-carboxylated polymer is a non-carboxylated polyacrylate polymer.

* * * * *